US009682144B2

(12) United States Patent
Thorin et al.

(10) Patent No.: US 9,682,144 B2
(45) Date of Patent: Jun. 20, 2017

(54) COMPOSITION COMPRISING INHIBITORS OF IRS-1 AND OF VEGF

(75) Inventors: Eric Thorin, Montreal (CA); Salman Al-Mahmood, Paris (FR); Sylvie Colin, Paris (FR); Antoine Ferry, Paris (FR); Eric Viaud, Lausanne (CH)

(73) Assignee: GENE SIGNAL INTERNATIONAL, SA (CH)

( * ) Notice: Subject to any disclaimer, the term of this patent is extended or adjusted under 35 U.S.C. 154(b) by 0 days.

(21) Appl. No.: 14/130,246

(22) PCT Filed: Jun. 29, 2012

(86) PCT No.: PCT/EP2012/062773
§ 371 (c)(1),
(2), (4) Date: Dec. 30, 2013

(87) PCT Pub. No.: WO2013/001080
PCT Pub. Date: Jan. 3, 2013

(65) Prior Publication Data
US 2014/0134185 A1 May 15, 2014

Related U.S. Application Data

(63) Continuation-in-part of application No. 13/174,038, filed on Jun. 30, 2011.

(30) Foreign Application Priority Data

Jun. 30, 2011 (EP) ..................................... 11172238

(51) Int. Cl.
*A61K 39/395* (2006.01)
*C12N 15/113* (2010.01)
*A61K 45/06* (2006.01)

(52) U.S. Cl.
CPC .......... *A61K 39/3955* (2013.01); *A61K 45/06* (2013.01); *C12N 15/113* (2013.01); *C12N 2310/11* (2013.01)

(58) Field of Classification Search
CPC .............. A61K 39/3955; C12N 15/113; C12N 2310/11
See application file for complete search history.

(56) References Cited

U.S. PATENT DOCUMENTS

| | | | |
|---|---|---|---|
| 5,629,344 A | 5/1997 | Charlton et al. | 514/588 |
| 5,801,156 A | 9/1998 | Robinson et al. | 514/44 A |
| 5,814,620 A | 9/1998 | Robinson et al. | 514/44 A |
| 6,378,526 B1 | 4/2002 | Bowman et al. | 128/898 |
| 7,417,033 B2 | 8/2008 | Al-Mahmood | 514/44 A |
| 7,759,472 B2 | 7/2010 | Shima et al. | 536/23.1 |
| 7,855,184 B2 | 12/2010 | Al-Mahmood | 514/44 A |
| 7,902,163 B2 | 3/2011 | Bennett et al. | 514/44 R |
| 8,133,877 B2 | 3/2012 | Al-Mahmood et al. | 514/44 A |
| 8,580,947 B2 | 11/2013 | Al Mahmood | 536/24.5 |
| 2005/0222065 A1 | 10/2005 | Khachigian | 514/44 R |
| 2008/0293658 A1 | 11/2008 | Al-Mahmood | 514/44 A |
| 2010/0305189 A1 | 12/2010 | Al Mahmood | 514/44 A |
| 2011/0184043 A1 | 7/2011 | Lagos-Quintana et al. | 514/44 A |
| 2012/0136041 A1 | 5/2012 | Rodrigues et al. | 514/44 A |

FOREIGN PATENT DOCUMENTS

| | | |
|---|---|---|
| EP | 1 010 433 | 9/1998 |
| EP | 1 179 541 | 2/2002 |
| EP | 1 409 672 | 6/2002 |
| WO | 92/13083 | 8/1992 |
| WO | 96/35791 | 11/1996 |
| WO | WO 00/64946 | 11/2000 |
| WO | 02/103014 | 12/2002 |
| WO | WO 2007/140924 | 12/2007 |
| WO | WO 2008/108986 | 9/2008 |
| WO | WO 2011/005377 | 1/2011 |

OTHER PUBLICATIONS

Bock et al, "Antiangiogene Therapie am vorderen Augenabschnitt", Der Ophthalmologe, 2007, 104(4): 336-344.
Cursiefen et al, Congress of the German Society of Ophthalmology, 2008.
Cursiefen et al, European Society of Caract and Refractive surgery, 2008.
Danis et al, "Intravitreous anti-raf-1 kinase antisense oligonucleotide as an angioinhibitory agent in porcine preretinal neovascularization." Curr Eye Res., 2003, 26(1):45-54.
Henry et al, "Antiviral activity and ocular kinetics of antisense oligonucleotides designed to inhibit CMV replication" Invest Ophthalmol Vis Sci. Oct. 2001; vol. 42 No. 11 pp. 2646-2651.
International Search Report dated Oct. 22, 2012, in PCT application.
Jiang et al, "Characterization of multiple signaling pathways of insulin in the regulation of vascular endothelial growth factor expression in vascular cells and angiogenesis" J Biol Chem., 2003, 278(34):31964-71.
Kim et al., "Intraocular Distribution of 70-kDa dextran after subconjunctival injection in mice." Investigative Ophthalmology & Visual Science, 2002, 43(6):1809-16.
Leeds et al, "Pharmacokinetics of an antisense oligonucleotide injected intravitreally in monkeys" Drug Metab Dispos., 1998, 26(7):670-5.
Li et al., "Subconjunctival antisense oligonucleotides targeting TNF-alpha influence immunopathology and viral replication in murine HSV-1 retinitis" Graefes Arch Clin Exp Ophthalmol. Sep. 2008; vol. 246 No. 9 pp. 1265-1273.

(Continued)

*Primary Examiner* — Ruixiang Li
(74) *Attorney, Agent, or Firm* — Norton Rose Fulbright US LLP

(57) ABSTRACT

The present invention relates to a composition or kit of parts comprising an inhibitor of IRS-1 and an inhibitor of the VEGF pathway and to the use thereof for treating an angiogenic disease.

2 Claims, 5 Drawing Sheets

(56) References Cited

OTHER PUBLICATIONS

Milligan et al, "Current concepts in antisense drug design", J Med Chem., 1993,36(14):1923-37.
Nolan et al, "Differential roles of IRS-1 and SHC signaling pathways in breast cancer cells", Int J Cancer, 1997,72(5):828-34.
Robinson et al. "Oligodeoxynucleotides inhibit retinal neovascularization in a murine model of proliferative retinopathy", Proc Natl Acad Sci U S A., 1996, 9(10):4851-6.
Surmacz et al, "Overexpression of insulin receptor substrate 1 (IRS-1) in the human breast cancer cell line MCF-7 induces loss of estrogen requirements for growth and transformation", Clin Cancer Res., 1995,1(11):1429-36.
Wallace et al, "Amyloid precursor protein requires the insulin signaling pathway for neurotrophic activity", Brain Res Mol Brain Res. 1997, 52(2):213-27.
Yanagi et al., "Subconjunctival administration of bucillamine suppresses choroidal neovascularization in rat" investigative ophthalmology & visual science, 2002, 43(11):3495-9.
Al-Mahmood et al., "Potent in Vivo Antiangiogenic Effects of GS-101 (5'- TATCCGGAGGGCTCGCCATGCTGCT-3'), an Antisense Oligonucleotide Preventing the Expression of Insulin Receptor Substrate-1," *J Pharmacol Exp Ther*, 329:496-504, 2009.
Berdugo et al., "Downregulation of IRS-1 expression causes inhibition of corneal angiogenesis," *Investigate Opthalmology & Visual Science*, 46(11):4072-4078, 2005.
Bradley et al., "Combination therapy for the treatment of ocular neovascularization," *Angiogenesis*, 10(2):141-148, 2007.
Cursiefen et al., "GS-101 antisense oligonucleotide eye drops inhibit corneal neovascularization: interim results of a randomized phase II trial," *Opthalmology*, 116:1630-1637, 2009.
Senthil et al., "The type 2 vascular endothelial growth factor receptor recruits insulin receptor substrate-1 in its signalling pathway," *Biochemical Journal*, 368(1):49-56, 2002.
D'Ambrosio et al. "Transforming potential of the insulin receptor substrate 1" Cell growth and differentiation, 1995, 6(5):557-562.
Henry et al "Setting sights on the treatment of ocular angiogenesis using antisense oligonucleotides" Trends in Pharmacological Sciences, 2004, 25(10):523-527.
Kain et al. "Tolerability and safety of GS-101 eye drops, an antisense oilgonucleotide to IRS-1: a first in man Phase I investigation." *Br J Clin Pharm* 68(2): 169-173, 2009.
Bochot et al. "Intravitreal admin of antisense oligonucleotides: potential of liposomal delivery.", *Prog in Retinal and Eye Res* 19(2): 131-146, 2000.
Hagigit et al. "Topical and intravitreous administration of cationic nanoemulsions to deliver antisense oligonucleotides directed towards VEGF KDR receptors to the eye.", *J Control Release.*, 145(3):297-305, 2010.
Reagan-Shaw, et al., "Dose translation from animal to human studies revisted," The FASEB Journal, vol. 22, Mar. 2007, pp. 659-661.

A

B

COMPOSITION COMPRISING INHIBITORS OF IRS-1 AND OF VEGF

CROSS-REFERENCE TO RELATED APPLICATIONS

This application is a national phase application under 35 U.S.C. §371 of International Application No. PCT/EP2012/062773 filed 29 Jun. 2012, which claims priority to European Patent Application No. 11172238.5 filed 30 Jun. 2011 and U.S. patent application Ser. No. 13/174,038 filed 30 Jun. 2011. The entire contents of each of the above-referenced disclosures is specifically incorporated herein by reference without disclaimer.

FIELD OF INVENTION

This invention relates to the treatment of angiogenic diseases, disorders or conditions. In particular, this invention relates to a kit of part or a composition comprising an inhibitor of the insulin receptor substrate-1 (IRS-1) and an inhibitor of the VEGF pathway, to prevent and/or treat diseases, disorders or conditions related to angiogenesis.

BACKGROUND OF INVENTION

Angiogenesis is a fundamental process by means of which new blood vessels are formed by endothelial cells. This formation involves three different steps, (i) the migration, (ii) the growth and (iii) the differentiation of endothelial cells.

Angiogenesis is essential in multiple normal physiological phenomena such as reproduction, development and even wound healing. In these normal biological phenomena, angiogenesis is under strict control, i.e., it is triggered during a short period (several days) and then completely inhibited. However, even though angiogenesis may be a normal physiological process, pathological neovascularization is a critical situation in a number of diseases, linked to the invasion of tissues and organs by neovessels. For example, invasive neovessels may damage the cartilage, causing arthritis. Moreover, about twenty different eye diseases are due to unregulated angiogenesis, such as diabetic retinopathy. Actually, the neovascularization of the ocular apparatus is a major cause of blindness. In the field of cancerology, the growth and metastasis of tumors are directly linked to neovascularization and thus dependent on angiogenesis. The tumor stimulates the growth of neovessels, which (i) allow the supply of nutrients and oxygen necessary to its growth, and (2) are escape routes for tumors, facilitating the dissemination of metastatic cells through the blood circulation.

An example of a protein involved in angiogenesis regulation is Insulin receptor substrate 1 (IRS-1), which is a cytoplasmic docking protein that functions as an essential signaling intermediate downstream of activated cell surface receptors, including insulin, insulin-like growth factor 1 (IGF-1), prolactin, growth hormone (GH), vascular endothelial growth factor (VEGF) receptors, members of the integrin receptor family, and cytokine receptors.

The inhibition of the expression of IRS-1 is thus a promising way to treat angiogenic diseases. For example, GS-101 (WHO INN Aganirsen), an insulin receptor substrate-1 (IRS-1) antisense oligonucleotide, was described in the European patent EP 1 409 672 as useful for inhibiting angiogenesis and for the treatment of eye diseases linked to neovascularization. Especially, GS-101 has been shown to prevent injury-associated corneal neovascularization (Al-Mahmood et al, 2009, J Pharmacol Exp Ther 329:496-504), and to regress proliferative corneal neovascularization in patients (Curseifen et al, 2009, Ophthalmology 116:1630-1637).

Vascular endothelial growth factor (VEGF) of sub-type A (VEGF-A) is a primary stimulant of angiogenesis. VEGF-A is a multifunctional cytokine which exists in several isoforms. Two of them are secreted (isoforms 121 and 165), corresponding to obligate dimers. VEGF dimers bind with high affinity to receptors VEGFR1 and VEGFR2, which are selectively expressed on endothelial cells.

Patent applications such as EP1 179 541 and WO2007/140924 describe that VEGF or VEGFR inhibitors can be used for treating angiogenic diseases. For example, Avastin® was approved by the FDA for treating cancer.

Surprisingly, the inventors found a synergic effect between the inhibition of IRS-1 and the inhibition of the VEGF pathway on the neovascularization process.

The present invention thus relates to an improved method for treating angiogenic diseases, disorders or conditions and more specifically ocular angiogenic diseases such as retinopathy, said method comprising the administration of an inhibitor of IRS-1 and an inhibitor of the VEGF pathway.

SUMMARY

The present invention thus relates to a composition comprising an inhibitor of IRS-1, preferably an inhibitor of IRS-1 expression and an inhibitor of the VEGF pathway.

The present invention also relates to a kit of part comprising an inhibitor of IRS-1 and an inhibitor of the VEGF pathway, wherein said kit of part comprises two parts, said first part comprising the inhibitor of IRS-1 and said second part comprising the inhibitor of the VEGF pathway.

In one embodiment, the inhibitor of IRS-1 is an inhibitor of the expression of IRS-1. Advantageously, said inhibitor of IRS-1 is an IRS-1 antisens oligonucleotide.

In one embodiment, the IRS-1 antisens oligonucleotide is a sequence of at least 12 nucleotides of SEQ ID NO: 1.

In one embodiment, the IRS-1 antisens oligonucleotide has the sequence SEQ ID NO: 2, or any function conservative sequence comprising from 9 to 50 nucleotides that has at least 75% of identity compared to SEQ ID NO: 2 and that conserves the capacity of inhibiting pathological neovascularization as SEQ ID NO: 2.

In one embodiment, said function conservative sequence is selected from the group comprising SEQ ID NO: 3 to SEQ ID NO: 21.

In one embodiment, the inhibitor of the VEGF pathway comprised in the composition or in the kit of part of the invention is an inhibitor of VEGF-A.

In one embodiment, the inhibitor of the VEGF pathway is an antibody directed to VEGF, preferably an antibody directed to VEGF-A.

In one embodiment, the inhibitor of the VEGF pathway is an antagonist of a VEGF receptor, preferably an antagonist of the VEGF-A receptor VEGFR1 or VEGFR2, preferably an antagonist of VEGFR2.

In one embodiment, the inhibitor of the VEGF pathway is an antibody directed to a VEGF receptor (VEGF-R), preferably an antibody directed to the VEGF-A receptor VEGFR1 or VEGFR2, more preferably an antibody directed to VEGFR2.

The present invention also relates to a pharmaceutical composition comprising the composition or the kit of part of the invention and a pharmaceutically acceptable excipient.

The present invention also relates to a medicament comprising the composition or the kit of part of the invention.

In one embodiment, the composition, the kit of part, the pharmaceutical composition or the medicament of the invention are for treating an angiogenic disease.

In one embodiment, the angiogenic disease is an ocular angiogenic disease.

In one embodiment, the angiogenic disease is cancer.

DEFINITIONS

In the present invention, the following terms have the following meanings:

"Pharmaceutically acceptable excipient": an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by FDA Office of Biologics standards.

"Intraocular administration": injection of a product directly in the interior of the eye, wherein the interior of the eye means any area located within the eyeball, and which generally includes, but is not limited to, any functional (e.g. for vision) or structural tissues found within the eyeball, or tissues or cellular layers that partially or completely line the interior of the eyeball. Specific examples of such areas include the anterior chamber, the posterior chamber, the vitreous cavity, the choroid, the macula, and the retina, and blood vessels and nerves which vascularize or innervate a posterior ocular region or site. According to a preferred embodiment, interior of the eye means the posterior segment of the eye, including the posterior chamber, the vitreous cavity, the choroid, the macula, and the retina, and blood vessels and nerves which vascularize or innervate a posterior ocular region or site. According to this preferred embodiment, the intraocular administration refers to an administration within the posterior segment of the eye, preferably within the vitreous, and the intraocular administration is more preferably an intravitreal injection.

"Topical administration": characterize the delivery, administration or application of a composition directly to the site of interest (e.g. the eye) for a localized effect. Preferably, topical administration is effected without any significant absorption of components of the composition into the subject's blood stream (to avoid a systemic effect).

"Antibody": (also known as immunoglobulins, abbreviated Ig) gamma globulin proteins that are found in blood or other bodily fluids of vertebrates, and are used by the immune system to identify and neutralize foreign objects, such as bacteria and viruses. Antibodies consist of two pairs of polypeptide chains, called heavy chains and light chains that are arranged in a Y-shape. The two tips of the Y are the regions that bind to antigens and deactivate them. The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

As used herein, the term antibody may also refer to an "antibody fragment", wherein an antibody fragment comprises a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments. The phrase "functional fragment or analog" of an antibody is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, Fc[epsilon]RI. Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')2 fragment that roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments that have hinge cysteines between them. Other chemical couplings of antibody fragments are also known.

"Chimeric antibody": an antibody comprising portions derived from different origins, joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain).

"Humanized antibody": an antibody comprising portions of antibodies of different origin, wherein at least one portion is of human origin. The same way, a "primatized antibody" is an antibody comprising portions of antibodies of different origin, wherein at least one portion is of primate origin.

"Treating": preventing (i.e. keeping from happening), reducing or alleviating at least one adverse effect or symptom of a disease, disorder or condition associated with a deficiency in or absence of an organ, tissue or cell function.

"Therapeutically effective amount": the amount of a therapeutic agent necessary and sufficient for (i) slowing down or stopping the progression, aggravation, or deterioration of one or more symptoms of the disease or condition; (ii) alleviating the symptoms of the disease or condition; or (iii) curing or treating the disease or condition.

DETAILED DESCRIPTION

The present invention relates to a composition comprising an inhibitor of IRS-1 and an inhibitor of the VEGF pathway.

The present invention relates to a composition comprising a therapeutically effective amount of an inhibitor of IRS-1 and a therapeutically effective amount of an inhibitor of the VEGF pathway.

According to a further embodiment, the composition of the invention consists of an inhibitor of IRS-1 and an inhibitor of the VEGF pathway.

The invention also relates to a kit of parts comprising the composition of the invention, and preferably comprising two parts. According to an embodiment, a first part of the kit comprises an inhibitor of IRS-1, and a second part comprises an inhibitor of the VEGF pathway.

The present invention also relates to a pharmaceutical composition comprising the composition or the kit of parts here-above described, and a pharmaceutically acceptable excipient.

The present invention also relates to a medicament comprising the composition or the kit of parts of the invention.

In one embodiment of the invention, said inhibitor of IRS-1 is not an inhibitor of IGF-1 signalling that is capable of reducing IRS-1 phosphorylation as described in WO2008/108986.

According to an embodiment, the inhibitor of IRS-1 is an inhibitor of the expression of IRS-1. Examples of inhibitors of the expression of IRS-1 include, but are not limited to, siRNAs, shRNAs, antisense oligonucleotide, ribozymes or aptamers of IRS-1.

According to another embodiment, the inhibitor of IRS-1 is an inhibitor of the activity of IRS-1. Examples of inhibitors of the activity of IRS-1 include, but are not limited to, the substances described in EP1 010 433.

According to an embodiment, said inhibitor of IRS-1 is an (IRS-1) antisense oligonucleotide.

According to an embodiment, the IRS-1 antisens oligonucleotide is a sequence of at least 12 nucleotides of SEQ ID NO: 1: 5'-TAGTACTCGAGGCGCGCCGGGCCCCCA-GCCTCGCTGGCCGCGCGCAGTACGAA GAAGCGTTTGTGCATGCTCTTGGGTTTGCGCAGG-TAGCCCACCTTGCGCACGTC CGAGAAGC-CATCGCTCTCCGGAGGGCTCGCCATGCTGCCACCG-3'. In one embodiment, the IRS-1 antisens oligonucleotide is a sequence of at least 12 contiguous nucleotides of SEQ ID NO: 1, preferably at least 13, 14, 15, 16, 17, 18, 19, 20, 21, 22, 23, 24, 25, 26, 27, 28, 29, 30 contiguous nucleotides of SEQ ID NO: 1.

According to an embodiment, the IRS-1 antisens oligonucleotide is GS-101. According to the invention, GS-101 is an antisens oligonucleotide having the sequence SEQ ID NO: 2,

5'-TCTCCGGAGGGCTCGCCATGCTGCT-3' or any function conservative sequence comprising from 9 to 50, 15 to 45, 20 to 40, 25 to 30 nucleotides that has 75%, 80%, 85%, 90%, 95% or more than 95%, 96%, 97%, 98%, 99% of identity compared to SEQ ID NO: 2 and that conserves the capacity of inhibiting pathological neovascularization as SEQ ID NO: 2.

The term "identity" or "identical", when used in a relationship between the sequences of two or more nucleotidic sequences, refers to the degree of sequence relatedness between nucleotidic sequences, as determined by the number of matches between strings of two or more bases. "Identity" measures the percent of identical matches between the smaller of two or more sequences with gap alignments (if any) addressed by a particular mathematical model or computer program (i.e., "algorithms"). Identity of related nucleotidic sequences can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. MoI. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

An example of a function conservative sequence of SEQ ID NO: 2 is SEQ ID NO: 3 (5'-TATCCGGAGGGCTCGC-CATGCTGCT-3'). Other examples of a function conservative sequence of SEQ ID NO: 2 are the following sequences:

| | |
|---|---|
| 5'-TCTCCGGAGGGCTCGCCATGCTGC-3' | (SEQ ID NO: 4) |
| 5'-TCTCCGGAGGGCTCGCCATGCTG-3' | (SEQ ID NO: 5) |
| 5'-TCTCCGGAGGGCTCGCCATGCT-3' | (SEQ ID NO: 6) |
| 5'-TCTCCGGAGGGCTCGCCATGC-3' | (SEQ ID NO: 7) |
| 5'-TCTCCGGAGGGCTCGCCATG-3' | (SEQ ID NO: 8) |
| 5'-TCTCCGGAGGGCTCGCCAT-3' | (SEQ ID NO: 9) |
| 5'-CTCCGGAGGGCTCGCCATGCTGCT-3' | (SEQ ID NO: 10) |
| 5'-TCCGGAGGGCTCGCCATGCTGCT-3' | (SEQ ID NO: 11) |
| 5'-CCGGAGGGCTCGCCATGCTGCT-3' | (SEQ ID NO: 12) |
| 5'-CGGAGGGCTCGCCATGCTGCT-3' | (SEQ ID NO: 13) |
| 5'-GGAGGGCTCGCCATGCTGCT-3' | (SEQ ID NO: 14) |
| 5'-GAGGGCTCGCCATGCTGCT-3' | (SEQ ID NO: 15) |
| 5'-AGGGCTCGCCATGCTGCT-3' | (SEQ ID NO: 16) |
| 5'-GGCTCGCCATGCTGCT-3' | (SEQ ID NO: 17) |
| 5'-GCTCGCCATGCTGCT-3' | (SEQ ID NO: 18) |
| 5'-CTCGCCATGCTGCT-3' | (SEQ ID NO: 19) |
| 5'-TCGCCATGCTGCT-3' | (SEQ ID NO: 20) |
| 5'-CGCCATGCTGCT-3'. | (SEQ ID NO: 21) |

According to an embodiment, said function conservative sequence of 25, 30, 35, 40, 45 or 50 nucleotides may be a sequence comprising SEQ ID NO: 2 or SEQ ID NO: 3 between other nucleic acids in C-terminal and N-terminal.

Said function conservative sequence may also be a 9 to 12 contiguous nucleotides fragment of SEQ ID NO: 2 or SEQ ID NO: 3.

According to an embodiment, the inhibitor of IRS-1, as here-above described, is present in the composition of the invention in a concentration of about 0.01 mg/ml to about 100 mg/ml, preferably 0.05 mg/ml to 80 mg/ml, more preferably 0.1 to 50 mg/ml, even more preferably about 0.5 mg/mL.

According to an embodiment, the inhibitor of the VEGF pathway may be an antibody directed to VEGF or VEGF receptor, or a fragment thereof; a soluble peptide that inhibit the activity of a VEGF receptor; a small molecule inhibitor, such as, for example, a small molecule inhibitor of kinases and/or signaling pathways relevant for VEGF receptors signal transduction; and/or inhibitor of the VEGF or VEGF receptor expression, such as, for example, siRNAs, shRNAs, antisens oligonucleotides, ribozymes and the like.

According to an embodiment, the inhibitor of the VEGF pathway is an antibody directed to VEGF that inhibits VEGF interaction with its natural receptor. According to an embodiment, the anti-VEGF antibody is a monoclonal antibody, a polyclonal antibody, a chimeric antibody, a fully human antibody, a primatized antibody, a humanized antibody or an antigen-binding fragment thereof.

Examples of anti-VEGF antibodies include, but are not limited to, Bevacizumab (Avastin®), ranibizumab (Lucentis®), G6-31, B20-4.1, Aflibercept, KH902 VEGF receptor—Fc fusion protein, sFLT101, sFLT102, 4A5 antibody, 4E10 antibody, 5F12 antibody, VA01 antibody, BL2 antibody, G6-31 antibody and fragments thereof.

According to an embodiment, the inhibitor of the VEGF pathway is a soluble receptor of VEGF that inhibits VEGF interaction with its natural receptor. Human soluble VEGFR2 recombinant proteins have been recently described. These soluble receptor proteins contain only the seven extracellular IgG-like repeats, which comprise all the information necessary for ligand binding. According to an embodiment of the invention, the inhibitor of the VEGF pathway is a soluble VEGFR2 receptor.

According to an embodiment, the inhibitor of the VEGF pathway is an inhibitor of the expression of VEGF, such as, for example a siRNA against VEGF. Examples of siRNA against VEGF include, but are not limited to, bevasiranib.

According to an embodiment, the inhibitor of the VEGF pathway is an antagonist of the VEGF-R. Examples of antagonists of the VEGF receptor include, but are not limited to, PLG101, ganglioside GM3 and peptide B3.

According to an embodiment of the invention, the inhibitor of the VEGF pathway is an antibody directed to a VEGF receptor. According to an embodiment, said antibody against a VEGF receptor is a monoclonal antibody, a polyclonal antibody, a chimeric antibody, a primatized antibody, a humanized antibody, and/or an antigen-binding fragment thereof. According to an embodiment, the antibody against VEGF receptor is selected in the group comprising the antibodies of the 3E7, DC101 antibody, Mab 25 antibody, Mab 73 antibody, GV39M, 2C3, 11B5 and 7G3 groups, mixtures and antigen-binding fragments thereof.

According to an embodiment, the inhibitor of the VEGF pathway is an inhibitor of the expression of the VEGF receptor, such as, for example a siRNA against VEGF-R. Examples of siRNA against VEGF-R include, but are not limited to, siRNA-027.

According to an embodiment, the inhibitor of the VEGF pathway is an inhibitor of kinases and/or signaling pathways relevant for VEGF receptors signal transduction. Examples of such inhibitors include, but are not limited to, decursin, decursinol, picropodophyllin, guggulsterone, eicosanoid LXA4, PTK787, pazopanib, axitinib, CDDO-Me, CDDO-1 mm, TG100801, sorafenib, and a pharmaceutically acceptable salt thereof.

According to an embodiment, the inhibitor of the VEGF pathway is an inhibitor of the VEGF-A pathway. VEGF is a glycoprotein which exhibits seven sub-types: VEGF A to E, and PlGF (placenta growth factor) 1 and 2. VEGF-A is the only one form of VEGF involved in angiogenesis.

According to a further embodiment, the inhibitor of the VEGF-A pathway is an inhibitor of a VEGF-A receptor.

Preferably, the inhibitor of the VEGF-A pathway is an inhibitor of VEGFR1 or VEGFR2, both receptors selectively expressed on endothelial cells and known as involved in angiogenesis. VEGFR1 and VEGFR2 bind the VEGF dimers formed by VEGF-A isomers 121 and 165. VEGFR1 (encoded by the FLT-1 gene) and VEGFR2 (encoded by the KDR/Flk-1 gene) are members of the Type III receptor tyrosine kinase (RTK III) family that is characterized by seven extracellular IgG-like repeats, a single spanning transmembrane domain and an intracellular split tyrosine kinase domain.

In an embodiment of the present invention, the inhibitor of the VEGF pathway is an inhibitor of VEGFR2 receptor. Preferably, the inhibitor of VEGFR2 receptor does not inhibit the VEGFR1 receptor.

According to a preferred embodiment of the invention, the inhibitor of the VEGF pathway is an antibody against VEGFR2 receptor. Examples of antibodies against VEGFR2 receptor and methods for identifying thereof are described in EP1 179 541 and in WO2011/005377, which are incorporated herein by reference. According to an embodiment, the antibody against VEGFR2 receptor is the monoclonal antibody 2C3 (ATCC PTA 1595), the monoclonal antibody DC101 or the antigen-binding fragment thereof.

According to an embodiment, the antibody against VEGFR2 receptor or antigen-binding fragment thereof is an unconjugated or naked antibody, which meant that is not attached to another agent, particularly a therapeutic or diagnostic agent. This definition does not exclude modifications of the antibody, such as, for example, modifications to improve the biological half-life, affinity, avidity or other properties of the antibody, or combinations of the antibody with other effectors.

According to another embodiment, the antibody against VEGFR2 receptor or antigen-binding fragment thereof is operatively attached to a therapeutic agent, the antibody against VEGFR2 receptor or antigen-binding fragment thereof and the therapeutic agent forming an immunoconjugate.

According to an embodiment, the therapeutic agent attached to the antibody against VEGFR2 receptor is an anti-angiogenic agent. Examples of anti-angiogenic agents include, but are not limited to angiostatin, endostatin, any one of the angiopoietins, vasculostatin, canstatin and maspin.

According to an embodiment, the therapeutic agent attached to the antibody against VEGFR2 receptor is a cytotoxic, cytostatic or otherwise anti-cellular agent that has the ability to kill or suppress the growth or cell division of endothelial cells. Suitable anti-cellular agents include chemotherapeutic agents, as well as cytotoxins and cytostatic agents. Cytostatic agents are generally those that disturb the natural cell cycle of a target cell, preferably so that the cell is taken out of the cell cycle. Some examples of chemotherapeutic agents include, but are not limited to, steroids;

cytokines; anti-metabolites, such as, for example, cytosine arabinoside, fluorouracil, methotrexate or aminopterin; anthracyclines; mitomycin C; vinca alkaloids; antibiotics; demecolcine; etoposide; mithramycin; and anti-tumor alkylating agents, such as, for example, chlorambucil or melphalan. Certain preferred anti-cellular agents are DNA synthesis inhibitors, such as daunorubicin, doxorubicin, adriamycin, and the like.

According to an embodiment, the therapeutic agent attached to the antibody against VEGFR2 receptor is a toxin moiety which delivers a cell killing effect. Examples of toxin moieties include, but are not limited to plant-, fungus- or bacteria-derived toxins. Examples of toxins include epipodophyllotoxins; bacterial endotoxin or the lipid A moiety of bacterial endotoxin; ribosome inactivating proteins, such as saporin or gelonin; a-sarcin; aspergillin; restrictocin; ribonucleases, such as placental ribonuclease; diphtheria toxin and pseudomonas exotoxin. Preferably, the toxin moiety is ricin A chain, deglycosylated ricin A, recombinant and/or truncated ricin A chain may also be used.

According to an embodiment, the therapeutic agent attached to the antibody against VEGFR2 receptor is an anti-tubulin drug. By "Anti-tubulin drug(s)", is meant any agent, drug, prodrug or combination thereof that inhibits cell mitosis, preferably by directly or indirectly inhibiting tubulin activities necessary for cell mitosis, preferably tubulin polymerization or depolymerization. Examples of anti-tubulin drugs include, but are not limited to, colchicine; taxanes, such as taxol; vinca alkaloids, such as vinblastine, vincristine and vindescine; and combretastatins, such as, for example, combretastatin A, B and/or D.

According to an embodiment, the therapeutic agent attached to the antibody against VEGFR2 receptor is a component that is capable of promoting coagulation, i.e., a coagulant or a coagulation factor. Preferred coagulation factors are Tissue Factor (TF) and TF derivatives, such as truncated TF (tTF), dimeric, trimeric, polymeric/multimeric TF, and mutant TF deficient in the ability to activate Factor VII. Other suitable coagulation factors include vitamin K-dependent coagulants, such as Factor II/IIa, Factor VII/VIIa, Factor IX/IXa and Factor X/Xa; vitamin K-dependent coagulation factors that lack the Gla modification; Russell's viper venom Factor X activator; platelet-activating compounds, such as thromboxane A2 and thromboxane A2 synthase; and inhibitors of fibrinolysis, such as alpha 2-antiplasmin.

According to an embodiment, the inhibitor of VEGF pathway, as here-above described, is present in the composition of the invention in a concentration of about 1 μg/ml to about 1000 μg/ml, preferably 5 μg/ml to 500 μg/ml, more preferably 10 to 100 μg/ml, even more preferably about 50 μg/mL.

According to an embodiment, the composition of the invention is sterile. Advantageously, it comprises a preservative in order to prevent the growth of microorganisms. The prevention of the action of microorganisms may be brought about by various antibacterial and antifungal agents, such as, for example, parabens, chlorobutanol, phenol, sorbic acid, thimerosal, and the like.

The composition, kit of part, pharmaceutical composition or medicament of the invention may be administered by several routes of administration. Examples of adapted routes of administration include, but are not limited to, subcutaneous, intramuscular, intravenous, intraocular, transdermal, topical, nasal and oral administration, or injection. The type of form for administration will be matched to the disease or disorder to be treated.

According to a preferred embodiment, the administration route is an ocular administration. According to a first embodiment, the administration route is a topical ocular administration, such as, for example, the administration of eye drops or by bathing the eye in an ophthalmic solution comprising the composition or the kit of part of the invention. According to a second embodiment, the administration route is an intraocular injection, such as, for example, an intravitreal and/or intracameral administration.

According to an embodiment, the composition, kit of part, pharmaceutical composition or medicament of the invention is in a form adapted for injection, preferably selected from the group comprising solutions, such as, for example, sterile aqueous solutions, dispersions, emulsions, suspensions, solid forms suitable for using to prepare solutions or suspensions upon the addition of a liquid prior to use, such as, for example, powder, liposomal forms and the like.

According to an embodiment, the composition, kit of part, pharmaceutical composition or medicament of the invention is in a form adapted to oral administration. According to a first embodiment, the form adapted to oral administration is a solid form selected from the group comprising tablets, pills, capsules, soft gelatin capsules, sugar-coated pills, orodispersing/orodispersing tablets, effervescent tablets or other solids. According to a second embodiment, the form adapted to oral administration is a liquid form, such as, for example, a drinkable solution, a buccal spray, liposomal forms and the like.

According to an embodiment, the composition, kit of part, pharmaceutical composition or medicament of the invention is in a form adapted for local delivery via the nasal and respiratory routes. Examples of formulations suitable for nasal administration include but are not limited to, nasal solutions, sprays, aerosols and inhalants.

According to an embodiment, the composition, kit of part, pharmaceutical composition or medicament of the invention is in a form adapted to topical administration. Examples of formulations adapted to topical administration include, but are not limited to, ointment, paste, eye drops, cream, patch, such as, for example, transdermal patch, gel, liposomal forms and the like.

According to an embodiment, the composition, kit of part, pharmaceutical composition or medicament of the invention is in the form of, or comprises, liposomes and/or nanoparticles.

According to an embodiment, the composition, kit of part, pharmaceutical composition or medicament of the invention further comprises some excipients, such as, for example, surfactants (e.g. hydroxypropylcellulose); suitable carriers, such as, for example, solvents and dispersion media containing, for example, water, ethanol, polyol (e.g. glycerol, propylene glycol, and liquid polyethylene glycol, and the like), suitable mixtures thereof, and vegetable oils, such as, for example, peanut oil and sesame oil; isotonic agents, such as, for example, sugars or sodium chloride; coating agents, such as, for example, lecithin; agents delaying absorption, such as, for example, aluminum monostearate and gelatin; preservatives, such as, for example, benzalkonium chloride, benzethonium chloride, chlorobutanol, thimerosal and the like; buffers, such as, for example, boric acid, sodium and potassium bicarbonate, sodium and potassium borates, sodium and potassium carbonate, sodium acetate, sodium biphosphate and the like; tonicity agents, such as, for example, dextran 40, dextran 70, dextrose, glycerin, potassium chloride, propylene glycol, sodium chloride; antioxidants and stabilizers, such as, for example, sodium bisulfite, sodium metabisulfite, sodium thiosulfite, thiourea and the like; nonionic wetting or clarifying agents, such as, for example, polysorbate 80, polysorbate 20, poloxamer 282 and tyloxapol; viscosity modifying agents, such as, for example dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose; and the like.

According to an embodiment, both parts of the kit are administered by the same administration route, as hereabove described. According to another embodiment, the first and second part of the kit of parts are not administered by the same administration route.

According to an embodiment, each part of the kit of parts is independently adapted to topical administration, local delivery via the nasal and respiratory routes, oral administration or injection.

According to a first embodiment of the invention, the first and second parts of the kit of parts are administered simultaneously to a subject. According to a second embodiment of the invention, the first and second parts of the kit are administered sequentially to a subject.

According to an embodiment of the invention, the amount of the composition, kit of part, pharmaceutical composition or medicament of the invention administered ranges from 0.1 µL to 1 mL, preferably from 0.5 µL to 500 µL.

According to an embodiment, the composition is packaged in a container which can be adapted on a syringe. According to an embodiment, each part of the kit of part is independently packaged in a container which can be adapted on a syringe.

According to an embodiment, the composition or each part of the kit of parts is presented in dosage unit form. Advantageously, the dosage unit form is a container means, such as, for example, a vial, a test tube, a flask, a bottle, a syringe or other container means into which the composition or each part of the kit of part may be placed.

The present invention also relates to a device comprising the composition, kit of part, pharmaceutical composition or medicament as here-above described. According to an embodiment, the device is a syringe for injection.

According to an embodiment, the composition, the kit of parts, the pharmaceutical composition or the medicament of the invention are for use in treating an angiogenic disease, disorder or condition in a subject in need thereof.

According to an embodiment, the composition, the kit of parts, the pharmaceutical composition or the medicament of the invention are for treating an angiogenic disease, disorder or condition in a subject in need thereof.

By angiogenic disease, disorder or condition is meant a disease, disorder or condition associated with angiogenesis, preferably associated with invasive and uncontrolled angiogenesis and/or characterized by undesired, inappropriate, aberrant, excessive and/or pathological vascularization.

Examples of angiogenic disease, disorder or condition include, but are not limited to tumor vascularization, retinopathies, rheumatoid arthritis, Crohn's disease, atherosclerosis, hyperstimulation of the ovary, psoriasis, endometriosis associated with neovascularization, restenosis due to balloon angioplasty, tissue overproduction due to cicatrization, peripheral vascular disease, hypertension, vascular inflammation, Raynaud's disease and phenomena, aneurism, arterial restenosis, thrombophlebitis, lymphangitis, lymphedema, tissue cicatrization and repair, ischemia, angina, myocardial infarction, chronic heart disease, cardiac insufficiencies such as congestive heart failure, age-related macular degeneration and osteoporosis, any form of vascularized tumor; macular degeneration, including age-related macular degeneration; arthritis, including rheumatoid arthritis; atherosclerosis and atherosclerotic plaques; diabetic retinopathy and other retinopathies; thyroid hyperplasias, including Grave's disease; hemangioma; neovascular glaucoma; psoriasis, arteriovenous malformations (AVM), meningioma, venous occlusive disease, arterial occlusive disease, vascular restenosis, including restenosis following angioplasty, angiofibroma, dermatitis, endometriosis, hemophilic joints, hypertrophic scars, inflammatory diseases and disorders, pyogenic granuloma, scleroderma, synovitis, trachoma, vascular adhesions, abnormal proliferation of fibrovascular tissue, acne rosacea, acquired immune deficiency syndrome, artery occlusion, atopic keratitis, bacterial ulcers, Bechets disease, blood borne tumors, carotid obstructive disease, chemical burns, conditions associated with choroidal neovascularization, choroidal vasculopathy, chronic inflammation, chronic retinal detachment, chronic uveitis, chronic vitritis, contact lens overwear, corneal graft rejection, corneal neovascularization, corneal graft neovascularization, Crohn's disease, Eales disease, epidemic keratoconjunctivitis, fungal ulcers, Herpes simplex infections, Herpes zoster infections, hyperviscosity syndromes, Kaposi's sarcoma, leukemia, lipid degeneration, Lyme's disease, marginal keratolysis, Mooren ulcer, Mycobacteria infections other than leprosy, myopia, ocular neovascular disease, optic pits, Osler-Weber syndrome (Osler-Weber-Rendu, osteoarthritis, Pagets disease, pars planitis, pemphigoid, phylectenulosis, polyarteritis, post-laser complications, protozoan infections, pseudoxanthoma elasticum, pterygium keratitis sicca, radial keratotomy, retinal neovascularization, retinopathy of prematurity, retrolental fibroplasias, sarcoid, scleritis, sickle cell anemia, Sogrens syndrome, solid tumors, Stargarts disease, Steven's Johnson disease, arterial macroaneurysm, superior limbic keratitis, syphilis, systemic lupus, Terrien's marginal degeneration, toxoplasmosis, trauma, tumors of Ewing sarcoma, tumors of neuroblastoma, tumors of osteosarcoma, tumors of retinoblastoma, tumors of rhabdomyosarcoma, ulceritive colitis, vein occlusion, Vitamin A deficiency and Wegeners sarcoidosis, undesired angiogenesis associated with diabetes, parasitic diseases, abnormal wound healing, hypertrophy following surgery, burns, injury or trauma, inhibition of hair growth, inhibition of ovulation and corpus luteum formation, inhibition of implantation and inhibition of embryo development in the uterus, graft rejection, lung inflammation, nephrotic syndrome, preeclampsia, pericardial effusion, such as that associated with pericarditis, pleural effusion, edema associated with brain tumors, ascites associated with malignancies, Meigs' syndrome, lung inflammation, nephrotic syndrome, pericardial effusion and pleural effusion, a vascularized solid tumor, a metastatic tumor or metastases from a primary tumor, gastrointestinal, genitourinary, lymphoid, and pulmonary (small cell and non-small cell) cancers and cancer of neural crest cell origin such as colorectal cancer, lung cancer, such as non-small cell lung cancer and small cell lung cancer, melanoma, pheochromocytoma, neuroblastoma, pancreatic cancer, lymphoma, especially Burkitt, Hodgkins and Non-Hodgkins lymphoma, testicular cancer, mesothelioma, renal cell carcinoma, ovarian cancer and prostate cancer.

According to an embodiment, the composition, the kit of parts, the pharmaceutical composition or the medicament of the invention are for use for treating cancer or oncological diseases. Examples of cancer or oncological diseases include, but are not limited to, carcinoma, lymphoma, blastoma, sarcoma, leukemia, solid tumours, such as urogenital cancers (such as prostate cancer, renal cell cancers, bladder cancers), gynecological cancers (such as ovarian cancers, cervical cancers, endometrial cancers), lung cancer such as, for example, non-small cell lung cancer (NSCLC), gastrointestinal cancers (such as non-metastatic or metastatic colorectal cancers, pancreatic cancer, gastric cancer, oesophageal cancers, hepatocellular cancers, cholangiocellular cancers), head and neck cancer (e.g. head and neck squamous cell cancer), malignant glioblastoma, malignant mesothelioma, non-metastatic or metastatic breast cancer (e.g. hormone refractory metastatic breast cancer), malignant melanoma or bone and soft tissue sarcomas, and haematologic neoplasias, such as multiple myeloma, acute myelogenous leukemia, chronic myelogenous leukemia, myelodysplastic syndrome and acute lymphoblastic leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, renal cancer, vulval cancer, thyroid cancer, hepatic carcinoma, gastric cancer, melanoma, and various types of head and neck cancer.

According to an embodiment, the composition, the kit of parts, the pharmaceutical composition or the medicament of the invention are for use for treating ocular angiogenic diseases.

According to an embodiment, the ocular angiogenic disease is associated with retinal, peripheral retinal and/or choroidal neovascularization. Examples of such angiogenic diseases include, but are not limited to uveitis, choroiditis, choroidal vasculopathy, hypersensitive retinopathy, retinochoroiditis, chorioretinitis, retinal angiomatosis, retinal degeneration, macular degeneration, AMD, retinal detachment, retinal neovascularisation, proliferative vitreoretinopathy, retinopathy of prematurity (ROP), central serous chorioretinopathy, diabetic retinopathy, posterior segment trauma, retinal vascular pathologies, retinal telangiectesa, endophthalmitis, macular edema, radiation-induced retinopathy, cystoid macular edema, diabetic retinopathy, inflammatory pathologies of the retina, sickle cell anemia, sickle cell retinopathy, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, systemic pathologies with implications for the retina, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications.

According to an embodiment, the ocular angiogenic disease is associated with corneal neovascularization. Examples of such angiogenic diseases include, but are not limited to diabetic retinopathy, retinopathy of prematurity, corneal graft rejection, neovascular glaucoma and retrolental fibroplasia, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, trauma, rheumatoid arthritis, systemic lupus, polyarteritis, Wegeners sarcoidosis, Scleritis, Steven's Johnson disease, periphigoid radial keratotomy, and corneal graph rejection.

According to an embodiment, the ocular angiogenic disease is selected from the group comprising diseases associated with rubeosis (neovascularization of the angle) and diseases caused by the abnormal proliferation of fibrovascular or fibrous tissue including all forms of proliferative vitreoretinopathy, whether or not associated with diabetes.

According to an embodiment, the composition, the kit of parts, the pharmaceutical composition or the medicament of the invention is for treating an ophthalmological disease. Illustrative examples of ophthalmological diseases are listed below.

In one embodiment, the ophthalmological disease is age-related macular degeneration. Examples of age-related macular degeneration include non-neovascular (also known as "Dry") and neovascular (also known as "Wet") macular degeneration. In one embodiment the dry age-related macular degeneration is associated with the formation of drusen. Treating dry macular degeneration also encompasses treating an abnormality of the retinal pigment epithelium. Examples of abnormalities of the retinal pigment epithelium include geographic atrophy, non-geographic atrophy, focal hypopigmentation, and focal hyperpigmentation. Treating wet age-related macular degeneration also encompasses treating choroidal neovascularization or pigment epithelial detachment.

In one embodiment, the ophthalmological disease is polypoidal choroidal vasculopathy. Polypoidal choroidal vasculopathy is characterized by a lesion from an inner choroidal vascular network of vessels ending in an aneurysmal bulge or outward projection.

In one embodiment, the ophthalmological disease is a condition associated with choroidal neovascularization. Examples of conditions associated with choroidal neovascularization comprise a degenerative, inflammatory, traumatic or idiopathic condition. Treating a degenerative disorder associated with choroidal neovascularization also encompasses treating a heredodegerative disorder. Examples of heredodegerative disorders include vitelliform macular dystrophy, fundus flavimaculatus and optic nerve head drusen. Examples of degenerative conditions associated with choroidal neovascularization include myopic degeneration or angioid streaks. Treating an inflammatory disorder associated with choroidal neovascularization also encompasses treating ocular histoplasmosis syndrome, multifocal choroiditis, serpimnous choroiditis, toxoplasmosis, toxocariasis, rubella, Vogt-Koyanagi-Harada syndrome, Behcet syndrome or sympathetic ophthalmia. Treating a traumatic disorder associated with choroidal neovascularization also encompasses treating choroidal rupture or a traumatic condition caused by intense photocoagulation.

In one embodiment, the ophthalmological disease is hypertensive retinopathy.

In one embodiment, the ophthalmological disease is diabetic retinopathy. Diabetic retinopathy can be nonproliferative or proliferative diabetic retinopathy. Examples of non-proliferative diabetic retinopathy include macular edema and macular ischemia.

In one embodiment, the ophthalmological disease is sickle cell retinopathy.

In one embodiment, the ophthalmological disease is a condition associated with peripheral retinal neovascularization. Examples of conditions associated with peripheral retinal neovascularization include ischemic vascular disease, inflammatory disease with possible ischemia, incontinentia pigmenti, retinitis pigmentosa, retinoschisis or chronic retinal detachment.

Examples of ischemic vascular disease include proliferative diabetic retinopathy, branch retinal vein occlusion, branch retinal arteriolar occlusion, carotid cavernous fistula, sickling hemoglobinopathy, non-sickling hemoglobinopathy, IRVAN syndrome (retinal vasculitic disorder characterized by idiopathic retinal vasculitis, an aneurysm, and neuroretinitis), retinal embolization, retinopathy of prematurity, familial exudative vitreoretinopathy, hyperviscosity syndrome, aortic arch syndrome or Eales disease. Examples of sickling hemoglobinopathy include SS hemoglobinopathy and SC hemoglobinopathy. Examples of non-sickling hemoglobinopathy include AC hemoglobinopathy and AS hemoglobinopathy. Examples of hyperviscosity syndrome include leukemia, Waldenstrom macroglobulinemia, multiple myeloma, polycythemia or myeloproliferative disorder.

Treating an inflammatory disease with possible ischemia also encompasses treating retinal vasculitis associated with systemic disease, retinal vasculitis associated with an infectious agent, uveitis or birdshot retinopathy. Examples of systemic diseases include systemic lupus erythematosis, Behcet's disease, inflammatory bowel disease, sarcoidosis, multiple sclerosis, Wegener's granulomatosis and polyarteritis nodosa. Examples of infectious agents include a bacterial agent that is the causative agent for syphilis, tuberculosis, Lyme disease or cat-scratch disease, a virus such as herpesvirus, or a parasite such as *Toxocara canis* or *Toxoplasma gondii*. Examples of uveitis include pars planitis or Fuchs uveitis syndrome.

In one embodiment, the ophthalmological disease is retinopathy of prematurity. Retinopathy of prematurity can result from abnormal growth of blood vessels in the vascular bed supporting the developing retina.

In one embodiment, the ophthalmological disease is venous occlusive disease. Examples of venous occlusive disease include branch retinal vein occlusion and central retinal vein occlusion. A branch retinal vein occlusion can be a blockage of the portion of the circulation that drains the retina of blood. The blockage can cause back-up pressure in the capillaries, which can lead to hemorrhages and also to leakage of fluid and other constituents of blood.

In one embodiment, the ophthalmological disease is arterial occlusive disease. Examples of arterial occlusive disease include branch retinal artery occlusion, central retinal artery occlusion or ocular ischemic syndrome. A branch retinal artery occlusion (BRAO) can occur when one of the branches of the arterial supply to the retina becomes occluded.

In one embodiment, the ophthalmological disease is central serous chorioretinopathy (CSC). In one embodiment, CSC is characterized by leakage of fluid in the central macula.

In one embodiment, the ophthalmological disease is cystoid macular edema (CME). In one embodiment, CME affects the central retina or macula. In another embodiment, CME occurs after cataract surgery.

In one embodiment, the ophthalmological disease is retinal telangiectasia. In one embodiment, retinal telangiectasia is characterized by dilation and tortuosity of retinal vessels and formation of multiple aneurysms. Idiopathic JXT, Leber's miliary aneurysms, and Coats' disease are three types of retinal telangiectasias.

In one embodiment, the ophthalmological disease is arterial macroaneurysm.

In one embodiment, the ophthalmological disease is retinal angiomatosis In one embodiment, retinal angiomatosis occurs when the ocular vessels form multiple angiomas.

In one embodiment, the ophthalmological disease is radiation-induced retinopathy (RIRP). In one embodiment, RIRP may display symptoms such as macular edema and nonproliferative and proliferative retinopathy.

In one embodiment, the ophthalmological disease is rubeosis iridis. In another embodiment, rubeosis iridis results in the formation of neovascular glaucoma. In another embodiment, rubeosis iridis is caused by diabetic retinopathy, central retinal vein occlusion, ocular ischemic syndrome, or chronic retinal detachment.

In one embodiment, the ophthalmological disease is a neoplasm. Examples of neoplams include an eyelid tumor, a conjunctival tumor, a choroidal tumor, an iris tumor, an optic nerve tumor, a retinal tumor, an infiltrative intraocular tumor or an orbital tumor Examples of an eyelid tumor include basal cell carcinoma, squamous carcinoma, sebaceous carcinoma, malignant melanoma, capillary hemangioma, hydrocystoma, nevus or seborrheic keratosis. Examples of a conjunctival tumor include conjunctival Kaposi's sarcoma, squamous carcinoma, intraepithelial neoplasia of the conjunctiva, epibular dermoid, lymphoma of the conjunctiva, melanoma, pingueculum, or pterygium. Examples of a choroidal tumor include choroidal nevus, choroidal hemangioma, metastatic choroidal tumor, choroidal osteoma, choroidal melanoma, ciliary body melanoma or nevus of Ota. Examples of an iris tumor include anterior uveal metastasis, iris cyst, iris melanocytoma, iris melanoma, or pearl cyst of the iris. Examples of an optic nerve tumor include optic nerve melanocytoma, optic nerve sheath meningioma, choroidal melanoma affecting the optic nerve, or circumpapillary metastasis with optic neuropathy. Examples of a retinal tumor include retinal pigment epithelial (RPE) hypertrophy, RPE adenoma, RPE carcinoma, retinoblastoma, hamartoma of the RPE, or von Hippel angioma. Examples of an infiltrative intraocular tumor include chronic lymphocytic leukemia, infiltrative choroidopathy, or intraocular lymphoma. Examples of an orbital tumor include adenoid cystic carcinoma of the lacrimal gland, cavernous hemangioma of the orbit, lymphangioma of the orbit, orbital mucocele, orbital pseudotumor, orbital rhabdomyosarcoma, periocular hemangioma of childhood, or sclerosing orbital psuedotumor.

According to an embodiment, the subject to whom the composition, the kit of parts, the pharmaceutical composition or the medicament is administered is a mammal, preferably a human.

In an embodiment of the invention, the subject to whom the composition, the kit of parts, the pharmaceutical composition or the medicament is administered is at risk for developing or is affected, preferably is diagnosed, with an angiogenic disease, disorder or condition.

The present invention also relates to a method for treating an angiogenic disease, disorder or condition in a subject in need thereof, comprising the administration of a therapeutically effective amount of an inhibitor of IRS-1 and of an inhibitor of the VEGF pathway.

The present invention also relates to a method for treating an angiogenic disease, disorder or condition in a subject in need thereof, comprising the administration of a composition comprising or consisting of a therapeutically effective amount of an inhibitor of IRS-1 and of an inhibitor of the VEGF pathway as described here above.

The present invention also relates to a method for treating an angiogenic disease, disorder or condition in a subject in need thereof, comprising the administration of a kit of part comprising a therapeutically effective amount of an inhibitor of IRS-1 and of an inhibitor of the VEGF pathway as described here above.

EXAMPLES

The present invention is further illustrated by the following examples.

Example 1

Materials and Methods

Animal Procedures

Ischemic proliferative retinopathy has been induced in Sprague-Dawley rat pups (Charles River) according to a protocol approved by the Animal Care Committee of Hôpital Ste-Justine (Montreal, Canada), in conformity with the Association for Research in Vision and Ophthalmology's statement on the Use of Animals in Ophthalmic Research. Essentially, animals were housed in standard rectangular cages in a pathogen-free facility and maintained on a 12 h light-12 h dark cycle. The room temperature and relative humidity were fixed at 21° C. and 50% respectively. Rat chow (Teklad, Harland, USA) and water were available ad libitum. Food, water and cages were changed twice weekly. This facility is certified by the Canadian Council on Animal Care.

Experimental Design

The oxygen induced retinopathy (OIR) model (Penn et al, 1994; Sapieha et al, 2008) was used in order to induce an abnormal pre-retinal neovascularization. Newborn rats were exposed to hyperoxic conditions (vessel rarefaction phase) from postnatal day (P) 7 to P12 followed with exposure at normoxic conditions from P13 to P17 (vaso-proliferative phase). Newborn rats were treated with either GS-101 (0.5 µl, 0.5 µg/injection) and/or an antibody against VEGF (Lucentis®, provided by Novartis Pharmaceuticals Canada Inc., 0.5 µl, 25 ng/injection) by two intraocular injections (P13 and P15) during the proliferative phase in order to evaluate its anti-angiogenic effects on pre-retinal neovascularization at P18. The sequence of GS-101 (5'-TATCCG-GAGGGCTCGCCATGCTGCT-3', SEQ ID NO: 3) has been previously published (Al-Mahmood et al., 2009).

Labelling and Quantification of Retinal Neovascularization

At P18, animals were euthanized in a $CO_2$ chamber, and eyes harvested and fixed in a 4% paraformadehyde solution for histological preparations. Fixed retinas have been dissected, permeabilized with 100% methanol, and incubated with TRITC-labeled lectin (Sigma) (1/100) overnight at room temperature. Flat-mounts were visualized with fluorescence microscopy (Nikon Eclipse E800, Japan). The severity of retinopathy has been assessed at P18 using a retinal scoring system which evaluates the following criteria: blood vessel growth, blood vessel tufts, extra-retinal neovascularization, central vasoconstriction, retinal haemorrhage, and blood vessel tortuosity (Higgins, 1999). In addition, vascular tufts per se have been evaluated on retinal flat-mount.

Statistical Analysis

Statistical analysis was conducted using a one-way analysis of variance followed by a Bonferroni's multiple comparison test; analysis was performed using Prism. P<0.05 was considered statistically significant.

Results

Figure 1:
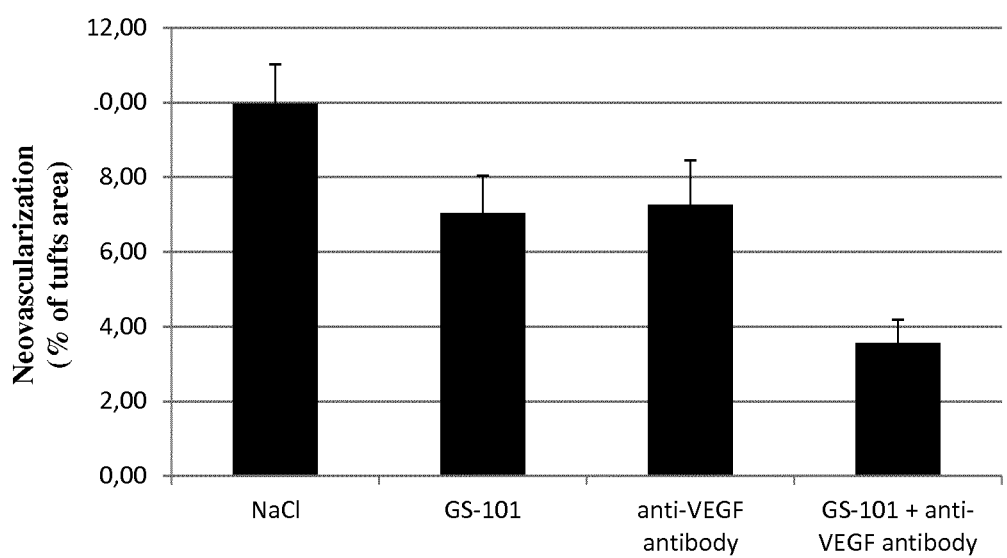
FIG. 1 is an histogram showing the neovascularization in rats treated with vehicle, GS-101, anti-VEGF antibody (Lucentis®) or with a combination of GS-101 and anti-VEGF antibody. Error bars are sem.

Individual data of quantification of retinal neovascularization after treatment with the vehicle (NaCl), GS-101, an anti-VEGF antibody or a combination of GS-101 and anti-VEGF antibody are presented in tables 1 to 4, and in FIG. 1.

Neovascularization in rats treated with NaCl is shown in table 1 (n=11)

TABLE 1

|      |       |
|------|-------|
|      | 7.03  |
|      | 9.70  |
|      | 9.96  |
|      | 12.46 |
|      | 9.99  |
|      | 13.57 |
|      | 7.17  |
|      | 7.74  |
|      | 14.19 |
|      | 3.16  |
|      | 4.55  |
| Mean | 9.95  |
| SEM  | 1.07  |

Neovascularization in rats treated with GS-101 (0.5 µg/injection) is shown in table 2 (n=11)

TABLE 2

|  |  |
|---|---|
|  | 11.64 |
|  | 8.01 |
|  | 5.00 |
|  | 2.47 |
|  | 3.08 |
|  | 7.79 |
|  | 0.87 |
|  | 10.61 |
|  | 6.01 |
|  | 8.36 |
|  | 6.37 |
| Mean | 7.02 |
| SEM | 1.01 |

Neovascularization in rats treated with an anti-VEGF antibody (25 ng/injection) is shown in table 3 (n=10)

TABLE 3

|  |  |
|---|---|
|  | 17.46 |
|  | 4.94 |
|  | 7.19 |
|  | 7.44 |
|  | 9.81 |
|  | 5.61 |
|  | 4.42 |
|  | 6.82 |
|  | 4.76 |
|  | 3.97 |
| Mean | 7.24 |
| SEM | 1.21 |

Neovascularization in rats treated with GS-101 and an anti-VEGF antibody (respectively 0.5 µg and 25 ng/injection) is shown in table 4 (n=11)

TABLE 4

|  |  |
|---|---|
|  | 3.70 |
|  | 5.30 |
|  | 1.70 |
|  | 6.22 |
|  | 3.60 |
|  | 6.99 |
|  | 2.59 |
|  | 1.15 |
|  | 1.28 |
|  | 2.19 |
|  | 0.63 |
| Mean | 3.54 |
| SEM | 0.65 |

The inhibition of neovascularization of each treatment (compared to the treatment with NaCl) is presented on table 5.

TABLE 5

|  | GS-101 | Anti-VEGF antibody | GS-101 + anti-VEGF antibody |
|---|---|---|---|
| Percent of neovascularization inhibition (compared to NaCl) | 29.43% | 27.21% | 65.00% |

These results demonstrate that the intraocular injection of GS-101 or of the anti-VEGF antibody both induce an inhibition of less than 30% of pathological retinal angiogenesis. The combined injection of GS-101 and of an anti-VEGF antibody induces an inhibition of 65% of the abnormal vascular proliferation.

Example 2

Materials and Methods

Animals, Cells, and Products

All the in vivo experiments were reviewed by the Genopole' institutional review board for laboratory animal care and use and were performed in accordance with the French national guidelines for animal care. The human lung tumor NCI-H460 (H460) cell line was purchased from American Type Culture Collection. Anti-IRS-1-HRP conjugate, anti-GAPDH-HRP conjugate, mouse anti-p-Erk1/2 (ref sc-7383), anti-p-Akt (Ser473, ref sc-7985-R), anti-goat-HRP conjugate antibodies were purchased from Santa Cruz, USA. A good manufactory practice batch of GS-101 (25mer phosphorothioate, molecular mass 8,036 Da; 5' TATCCG-GAGGGCTCGCCATGCTGCT3', SEQ ID NO: 3) was provided by the company Gene Signal (Al-Mahmood, 2002; Al-Mahmood et al., 2009) (Swiss Institute of Technology, Lausanne, Switzerland). The scramble phosphorothioate oligonucleotide (SO) used has the following sequence: 5'-TG-GACCTCTGGAGCTCTCGACGTGC-3', SEQ ID NO: 22).

Real-Time RT-PCR

H460 cells were grown in RPMI containing 10% FCS at 37° C. and 5% $CO_2$ humidified atmosphere. Cell layers were washed, incubated with serum-deprived culture medium overnight, and exposed to GS-101 (0-20 µM), SO (0-20 µM) or vehicle (0.9% NaCl) for 24 hr, followed by extraction of total mRNA from H460 cells ($5 \times 10^5$ cells/ml), or tumor blocks harvested at the end of the in vivo treatments, using NucleoSpin RNA II kit. RNA yields and purity were assessed, analyzed, and the real-time RT-PCR was performed as previously described (Al-Mahmood et al., 2009). The synthesized cDNA was used immediately for real-time PCR amplification using SYBR Green I for the detection of PCR products and the following primers: for h-VEGFA (5'GAGGGCAGAATCATCACGAA3', SEQ ID NO: 23 and 5'TGCTGTCTTGGGTGCATTGG3', SEQ ID NO: 24); h-GAPDH (5'TGAAGGTCGGAGTCAACGGA3', SEQ ID NO: 25; and 5'CATTGATGACAAGCTTCCCG3', SEQ ID NO: 26); m-VEGFA (5'TTGTCCAAGATCCGCAGACG3', SEQ ID NO: 27 and 5'TCGGTCTTTCCGGTGAGAGG3', SEQ ID NO: 28); m-GAPDH (5'AGCTCACTGGCATG-GCCTTC3', SEQ ID NO: 29 and 5'GAGGTCCACCAC-CCTGTTGC3', SEQ ID NO: 30). The real-time PCR reactions were carried out with the DNA Engine Opticon 2 continuous fluorescence detector (MJ Research, Waltham, Mass., U.S.A.). The results were quantified and all PCR products were analyzed as previously described (Al-Mahmood et al., 2009).

Protein Quantification

Serum-deprived H460 cells were incubated with different concentrations of GS-101 or SO at 37° C. under 5% $CO_2$ for 6 h. Cells were washed with ice-cold PBS, and taken with the protein extraction buffer (PEB) (Al-Mahmood et al., 2009). The protein content was adjusted, and IRS-1 protein, human VEGFA (h-VEGFA) and mouse VEGFA (m-VEGFA) were quantified in cell lysates, the culture medium of H460 cells, or in the plasma of mice by Sandwich ELISA kits (Cell Signaling Technology Inc., Danvers, Mass.) according to the manufacturer's instructions. Data were collected from 4 separate experiments performed in duplicate and expressed relative to control (cells treated with vehicle). IC$_{50}$ values were calculated with GraphPad Prism 5 using a nonlinear regression (Al-Mahmood et al., 2009). The adjusted cells lysates were also resolved by SDS-PAGE, and immunoblotted with anti-GAPDH-HRP conjugate, mouse anti-p-Erk1/2, or goat anti-p-Akt, and anti-goat-HRP conjugate were performed. Proteins were then monitored by ECLplus (GE Healthcare, Chalfont St. Giles, UK).

GS-101 In Vivo Bioavailability

H460 tumor cells (5×10$^6$ cells in 200 µL HBSS) were injected subcutaneously into the right flanks of mice (female BALB/c nu/nu mice, n=18) (Charles Rivers, France). Tumor volume (TV) was measured using a Vernier calliper, and calculated as described (Balsari et al., 2004). At TV≈10$^3$ mm$^3$, mice were injected intraperitoneally (i.p.) with 100 µL/injection of either vehicle (0.9% saline), or 400 µM GS-101. In preliminary experiments, tumor-bearing mice were dosed i.p. with increasing concentrations of GS-101, and 40 nmoles of GS-101 in 100 µL were chosen as it led to a targeted GS-101 concentration of ≈1 µM in the plasma. At the indicated time, three mice were either exsanguinated by decapitation (2 min time-point) or anesthetized i.p. with 100 µL ketamine and exsanguinated by cardiac puncture. Visceral organs and tumor blocks were harvested, weighed, flash frozen in liquid nitrogen, and stored at −80° C. until analyzed.

In Vivo Measurement of GS-101 Concentration by Noncompetitive Hybridization-Ligation ELISA Solid tissue or tumor blocks were homogenized in lysis buffer (Cell Signaling Technology Inc., Danvers, Mass.) at 4° C. for 30 min, and cleared at 16000 g for 10 min. GS-101 concentrations in plasma and tissue extracts were determined by noncompetitive hybridization-ligation ELISA assay. Briefly, 100 µL of template (Biotine-3'-ATAGGC-CTCCCGAGCGGTACGACGA-5' (complementary to GS-101 with 9 additional nucleotides 3'-AGCGATAAG-5', SEQ ID NO: 31) (Eurofins, Les Ulis, France) solution in the hybridization buffer (60 mM Na$_2$HPO$_4$ pH 7.4, 0.9 M NaCl and 0.24% Tween) (Eurogentec, Belgium) was incubated with plasma samples (100 µL) at 37° C. for 1 hr for hybridization in a polypropylene 96-well plate. After hybridization, 150 µL of the solution were transferred to a NeutrAvidin-coated 96-well plate (Pierce, Brebières, France) and incubated at 37° C. for 30 min. After four buffer washes, 150 µL of the ligation probe solution (Phosphate-5'-TCGC-TATTC-3'-digoxigenin) (MWG, Les Ulis, France) containing T4 DNA ligase (1.33 U/ml) and 0.05 mM ATP (Amersham Bioscience, Orsay, France) were added and incubated at 22° C. for 2 hr. The plate was then washed with the washing buffer (25 mM Tris-HCl pH 7.2, 0.15 M NaCl and 0.1% Tween), and deionized water. Subsequently, 150 µL of 1:10$^4$ diluted anti-digoxigenin-AP (Roche diagnostic, Meylan, France) were added and incubated at 22° C. for 0.5 hr. After washing with the washing buffer, AttoPhos (Promega Corporation, Charbonnieres, France) was added and the plate was incubated at 30° C. for 30 min. Optical density was determined at 450 nm using a µQuant micro-plate reader (BioTek Instruments, Colmar, France) coupled to the KC4 software (BioTek Instruments).

Tumor-Induced In Vivo Angiogenesis

For each plug, tumor cells (10$^6$ cells in 50 µL HBSS) were added to 450 µL of Matrigel (Becton Dickinson, USA), and the mixture was injected subcutaneously into the right flanks of mice (female BALB/c nu/nu mice, n=10). At day (D) 3, mice were randomized into two groups of 5 mice, and treatments were started by daily i.p. injections (100 µL/injection). Control mice were injected with vehicle (0.9% saline). Group 2 was injected with GS-101 (400 µM). At the end of treatments (D8 post inoculation), animals were anesthetized, and plugs were harvested, weighted and analyzed for hemaglobulin contents as previously described (Rice, 1967).

Tumor Xenografts in Nude Mice and GS-101 Administration

Female BALB/c nu/nu mice (n=14), 4-5 weeks aged were used. H460 cells (5×10$^6$ cells in 200 µL HBSS) were implanted subcutaneously into the right flanks of mice. At TV≈200 mm$^3$, animals were randomized, and separated into two groups. Treatments were realized by i.p. injections (100 µL/injection). Control mice were injected daily with vehicle (0.9% saline). In Group 2, mice were injected daily with GS-101 (400 µM). TV and body weight were measured every other day over the treatment period (11 days).

Statistical Analysis

Continuous data are presented as mean±sem, with "n" the number of independent experiments. Appropriate univariate analysis (t-test or ANOVA with Fisher's post hoc test) was used (Statview 4.5). A $p<0.05$ was considered statistically significant.

Results

Figure 2:
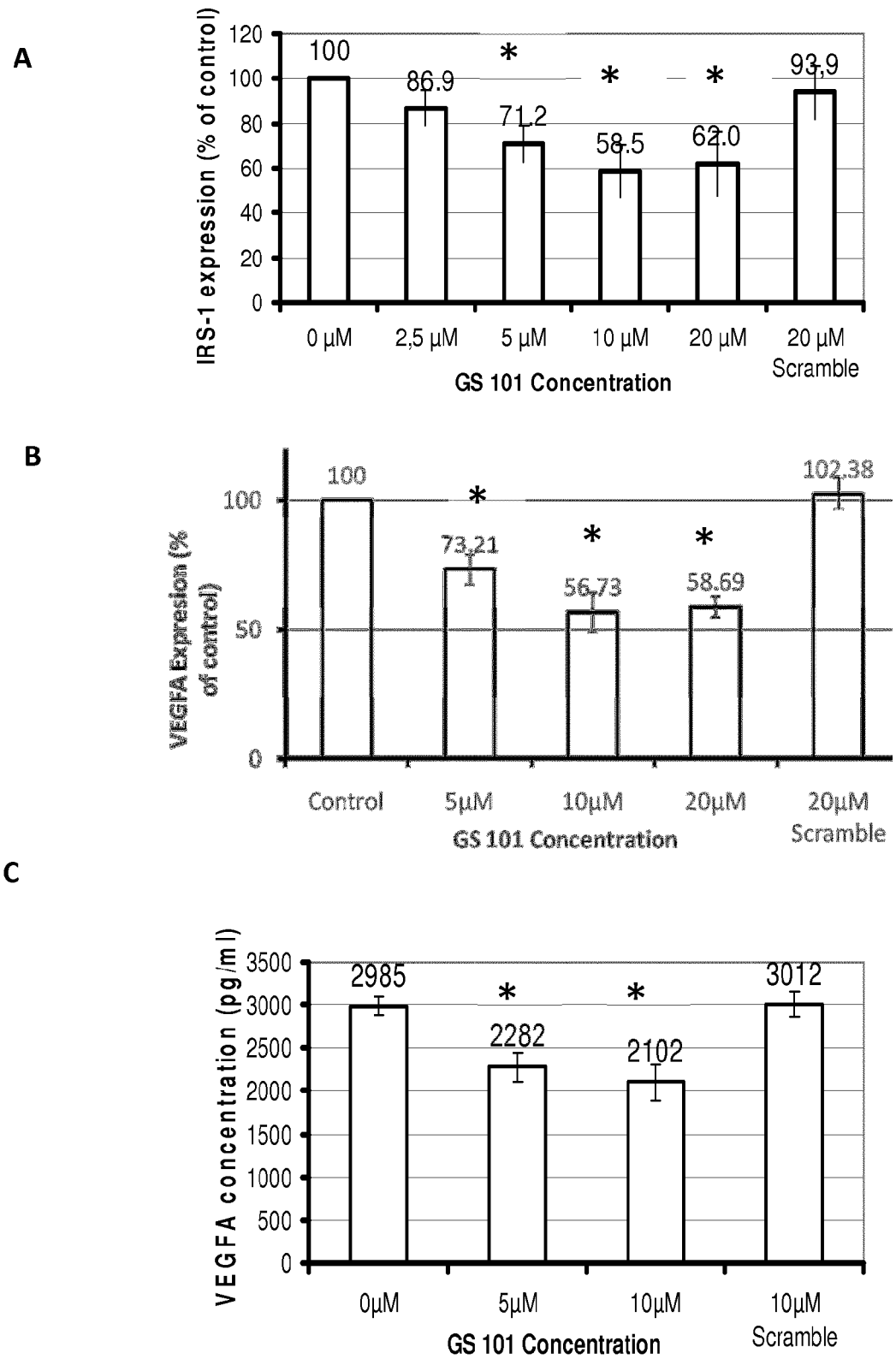
FIG. 2 is a combination of graphs showing the concentration-dependent inhibition of IRS-1 and VEGF expression in tumor cells by GS-101. Equivalent amounts of proteins extracts from H460 tumor cells were used to quantify IRS-1 protein by ELISA Sandwich assay (A); VEGFA expression by QPCR (B), and VEGFA protein in the culture medium of H460 tumor cells by ELISA Sandwich assay (C). Data were expressed as mean±SD and reported vs. vehicle (0.9% NaCl). As a control experiment, SO (20 µM) was used. *: P<0.05 versus control (vehicle-treated group, 0.9% NaCl).

To address the possible involvement of IRS-1 in tumor-induced angiogenesis, the human tumor cell line H460 was exposed to increasing concentrations of either SO or GS-101. Cellular proliferation was not significantly altered (−11±4% at confluence of untreated cells, $p<0.05$, n=6) in the presence of GS-101 (10 µM). In contrast to SO, GS-101 dose-dependently reduced IRS-1 expression with an IC$_{50}$ of 4.52±1.22 µM (n=4) (FIG. 2A); this reduction was paralleled with a concentration-dependent inhibition of both mRNA (IC$_{50}$=3.12±0.82 µM) (n=4) and protein expression of VEGFA in the culture medium (FIGS. 2B and C).

Figure 3:
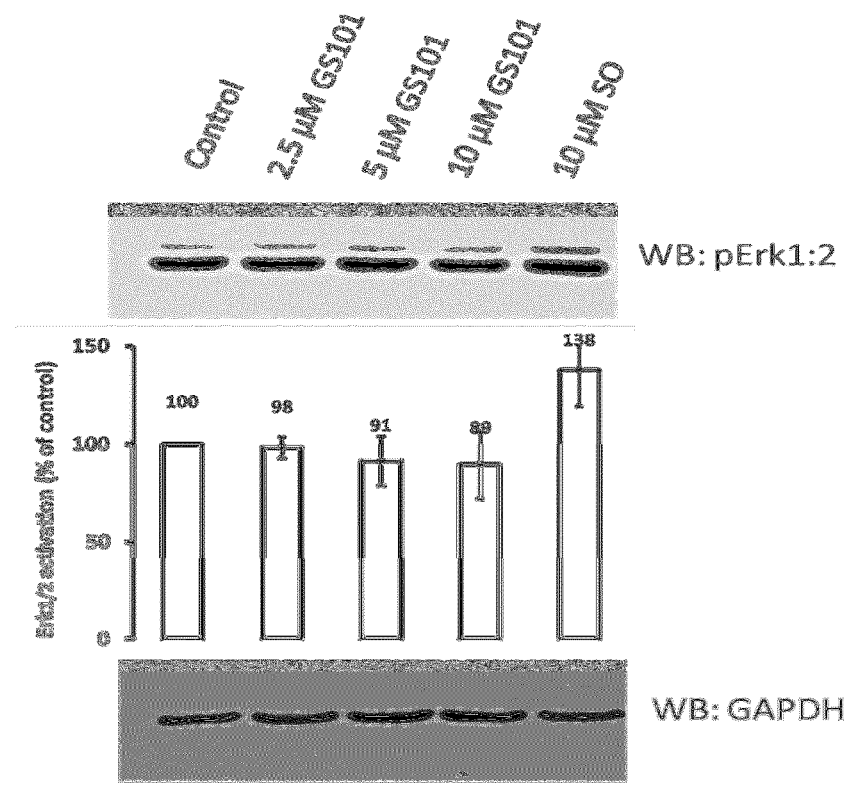
FIG. 3 is a combination of graphs and pictures, showing the effects of 4-hr exposure to GS-101 (0-10 µM) on p-Erk1/2 (A) and p-Akt (B) expression measured by Western blot. Equal protein loading was controlled for by GAPDH immunoblotting. As a negative control, SO was used (10 µM). Representative images of four independent experiments are presented. *: P<0.05 versus control (vehicle-treated group, 0.9% NaCl).
Figure 3:
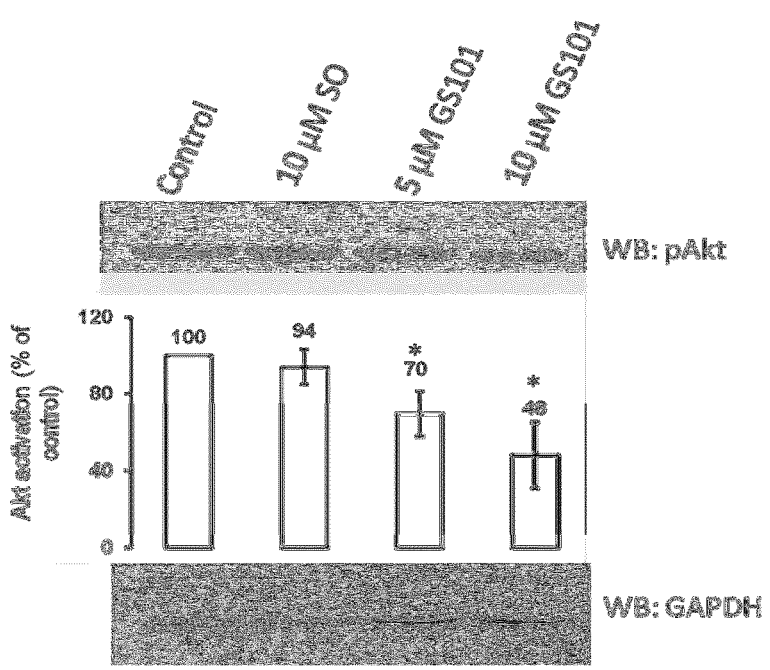

We also investigated the influence of SO and GS-101 on Akt and Erk1/2 activation. Following 4 hr of incubation of H460 with GS-101, no change in Erk1/2 activity was detectable (FIG. 3A); however GS-101 significantly decreased Akt activation (FIG. 3B).

GS-101 Inhibits Tumor-Induced In Vivo Angiogenesis.

Figure 4:
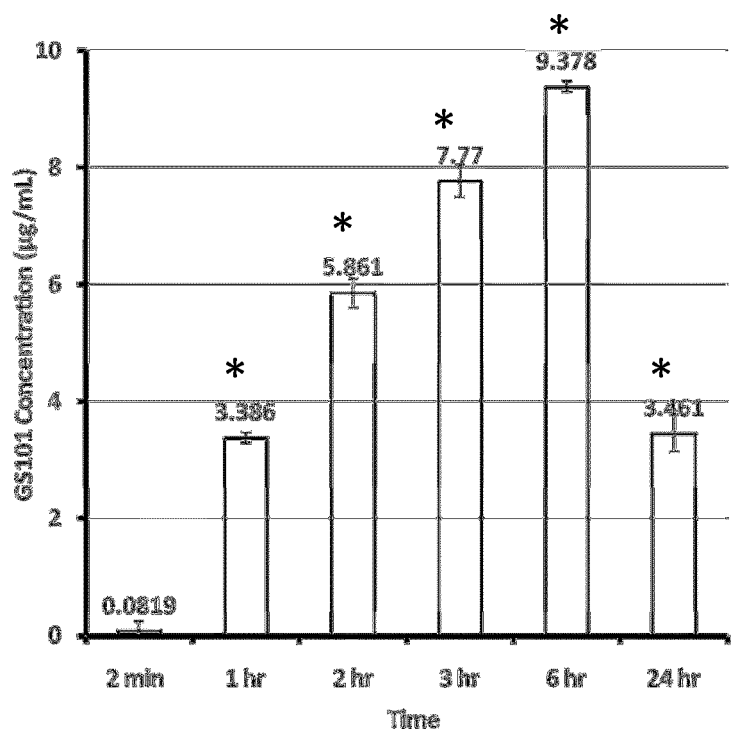
FIG. 4 is a combination of graphs and pictures showing the in vivo inhibition of tumor-induced angiogenesis by GS-101. A) Plasma concentration of GS-101 following a single intraperitoneal (i.p.) injection of 40 nanomoles in H460 tumor-bearing Nude mice. Data are expressed as mean±SD (n=3) and reported as µg GS-101/ml of plasma. B) Effects of GS-101 on tumor-induced in vivo angiogenesis monitored by the quantification of hemaglobulin in tumor-enriched Matrigel plugs, and expressed as g of hemaglobulin/ml of plug volume. Results are expressed as the mean±SEM, n=5. *: P<0.01 versus vehicle-treated group (0.9% NaCl).
Figure 4:
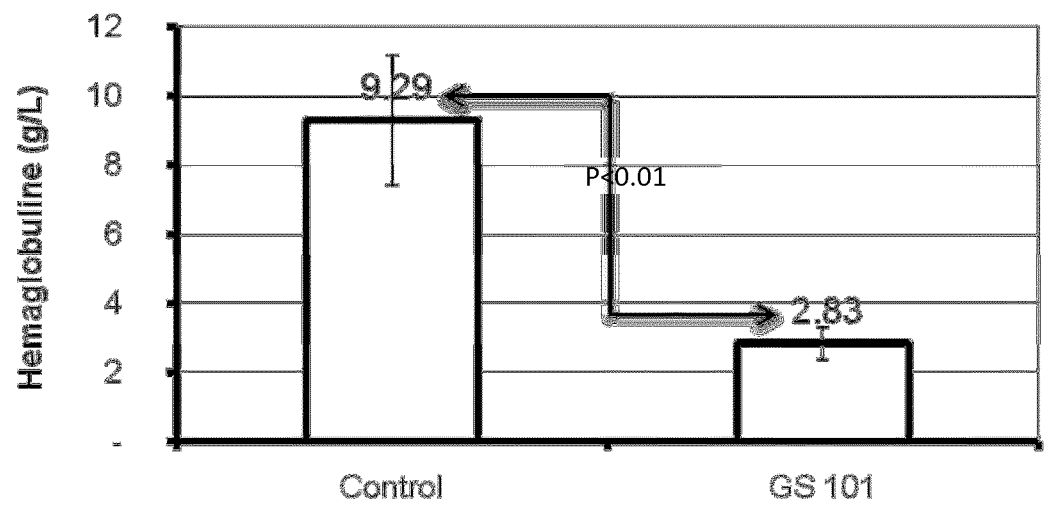

In preliminary experiments, tumor-bearing mice were dosed i.p. with increasing concentrations of GS-101, and 40 nmoles of GS-101 in 100 µL were chosen. Measurements of GS-101 concentrations indicate that a single i.p. injection of 400 µM GS-101 leads to a gradual increase in plasma concentration of GS-101 during the first hours reaching 9.378+0.056 µg/mL (i.e. about 1.166 µM) (n=3) at 6 hr (FIG. 4A), followed by the clearance of GS-101 as indicated by the drop in GS-101 plasma concentration at 24 hr post injection (FIG. 4A).

To quantify the influence of GS-101 on tumor-induced angiogenesis, we used Matrigel plugs enriched with H460 tumor cells implanted into Nude mice. At the end of treatments, while plugs isolated from the vehicle-treated group were homogenously red indicative of a strong hemoglobin load and thus vascularization, plugs isolated from the GS-101-treated group had a white-yellowish color with sporadic small red spots, indicating that GS-101 inhibited tumor-induced plug neovascularization (FIG. 4B). The quantification of hemoglobin showed indeed that in plugs isolated from GS-101-treated mice have 70±5% (n=5; $p<0.01$) less hemoglobin relative to vehicle-treated mice (FIG. 4B), suggesting that GS-101 potently inhibited tumor-induced angiogenesis in vivo.

GS-101 Inhibits Tumor Growth and Pathologic VEGFA Expression In Vivo.

Figure 5:
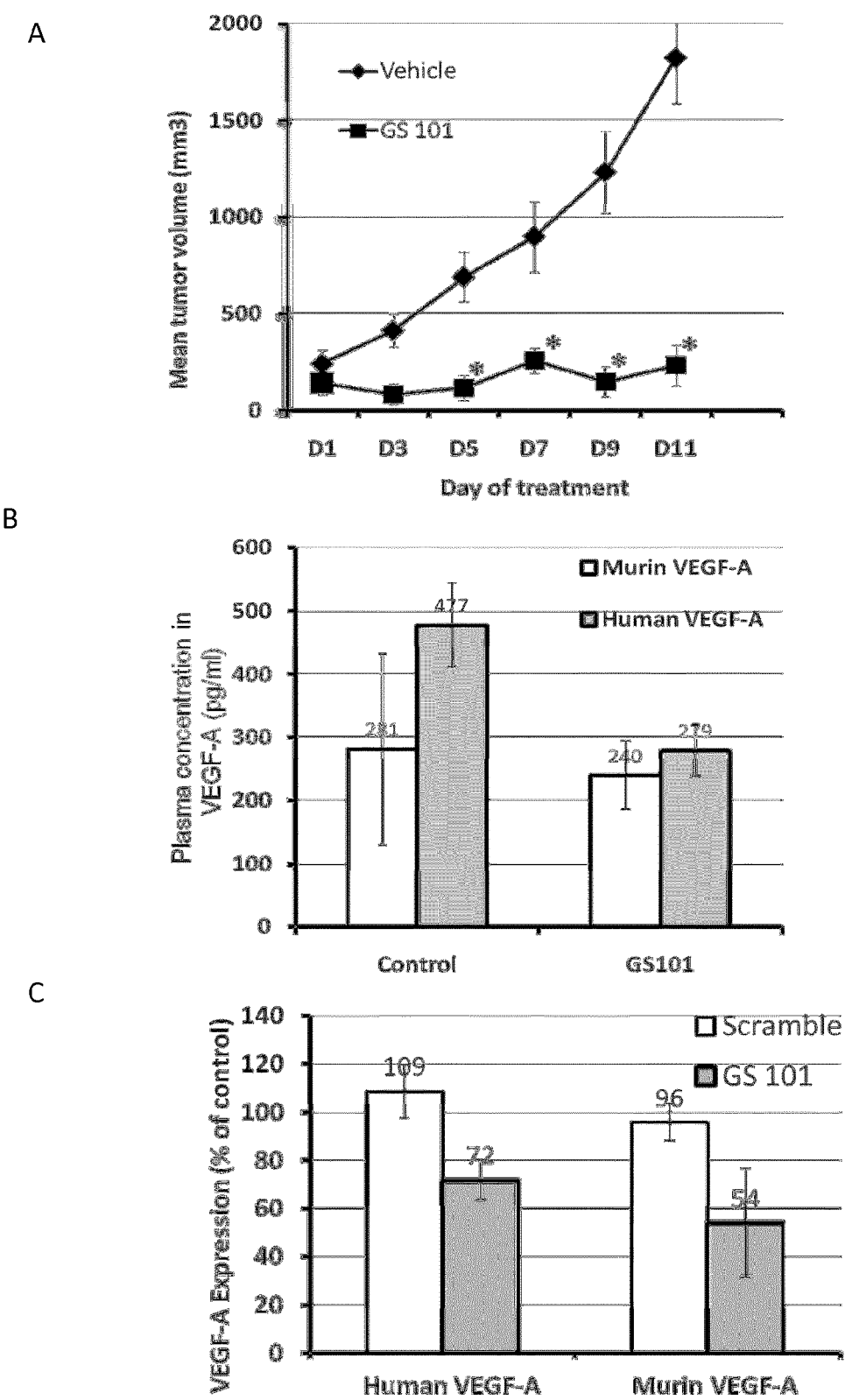
FIG. 5 is a combination of graphs showing that GS-101 inhibits in vivo tumor growth and tumor-derived human VEGFA (h-VEGFA) production, but not physiological mouse VEGFA (m-VEGFA). A) MTV evolution curves of mice bearing H460 tumors treated with the vehicle or GS-101 at a daily dose of 12.8 mg/kg. Data are expressed as mean±SEM (n=7). *: P<0.05 versus vehicle-treated group (0.9% NaCl). B) QPCR measurement of m- and h-VEFGA mRNA levels in tumor blocks at the end of the treatment with vehicle or GS-101. Data are expressed as mean±SEM (n=7). *: P<0.01 versus vehicle-treated group (0.9% NaCl). C) ELISA determination of circulating m- and h-VEFGA proteins at the end of treatment with vehicle or GS-101. Data are expressed as mean±SEM (n=7). *: P<0.01 versus vehicle-treated group (0.9% NaCl).

All nude mice were bearing H460 tumor at day 12, and survived during the therapy. Before therapy, there were no significant differences in bodyweight and tumor volumes. The results of mean tumor volume (MTV) are shown in FIG. 5A. Relative to MTV of vehicle-treated mice (1820.14±236.23 mm$^3$; n=7), MTV of GS-101-treated mice was lower at day 3 (p<0.05) and remained stable until the end of the treatment (FIG. 5A). The MTV of GS-101-treated mice were 258.18±66.21 and 232.54±108.33 mm$^3$ versus 897.26±183.45 and 1820.14±236.23 mm$^3$ in vehicle-treated mice at D7 and D11 of treatment, respectively; this represents a 71±7% and 87±6% inhibition of tumor growth at D7 and D11, respectively (n=7; p<0.01) (FIG. 5A).

At the end of treatments, tumor blocks were harvested. Quantification of mRNA of VEGFA indicates that GS-101 induced a 29±8% (n=7; p<0.05) and 46±20% (n=7; p<0.05) reduction in h-VEGFA and m-VEGFA transcripts expression, respectively (FIG. 5B).

The quantification of circulating m-VEGFA and h-VEGFA proteins at the end of treatments (FIG. 5C) indicates that there was no significant variation in m-VEGFA protein between vehicle- and GS-101-treated mice. However, the circulating h-VEGFA protein level was reduced by 42±6% (n=7; p<0.01) by the treatment with GS-101 (FIG. 5B).

The invention claimed is:

1. A method for treating an angiogenic disease comprising administering a synergistic therapeutically effective amount of an inhibitor of insulin receptor substrate-1 (IRS-1) expression and an inhibitor of vascular endothelial growth factor (VEGF) pathway,
   wherein the inhibitor of IRS-1 is an IRS-1 antisense oligonucleotide consisting of a sequence SEQ ID NO: 2, or any function conservative sequence of SEQ ID NO: 2 selected from the group consisting of SEQ ID NO: 3 to 21 and
   wherein the inhibitor of the VEGF pathway is the anti-VEGF antibody, ranibizumab, wherein:
   the synergistic therapeutically effective amount of the inhibitor of insulin receptor substrate-1 (IRS-1) is such that an amount of 0.5 μg may be administered to a subject in need thereof; and
   the synergistic therapeutically effective amount of an inhibitor of the anti-VEGF antibody, ranibizumab is such that an amount of 25 ng may be administered to a subject in need thereof.

2. The method of claim 1, wherein the angiogenic disease is an ocular angiogenic disease.

* * * * *

```
                              SEQUENCE LISTING

<160> NUMBER OF SEQ ID NOS: 31

<210> SEQ ID NO 1
<211> LENGTH: 150
<212> TYPE: DNA
<213> ORGANISM: Artificial Sequence
<220> FEATURE:
<223> OTHER INFORMATION: IRS-1 antisens

<400> SEQUENCE: 1
tagtactcga ggcgcgccgg gcccccagcc tcgctggccg cgcgcagtac gaagaagcgt      60
ttgtgcatgc tcttgggttt gcgcaggtag cccaccttgc gcacgtccga gaagccatcg     120
ctctccggag ggctcgccat gctgccaccg                                      150

<210> SEQ ID NO 2
<211> LENGTH: 25
<212> TYPE: DNA
<213> ORGANISM: Artificial Sequence
<220> FEATURE:
<223> OTHER INFORMATION: IRS-1 antisens

<400> SEQUENCE: 2
tctccggagg gctcgccatg ctgct                                            25

<210> SEQ ID NO 3
<211> LENGTH: 25
<212> TYPE: DNA
<213> ORGANISM: Artificial Sequence
<220> FEATURE:
<223> OTHER INFORMATION: IRS-1 antisens

<400> SEQUENCE: 3
tatccggagg gctcgccatg ctgct                                            25

<210> SEQ ID NO 4
<211> LENGTH: 24
<212> TYPE: DNA
<213> ORGANISM: Artificial Sequence
<220> FEATURE:
<223> OTHER INFORMATION: IRS-1 antisens

<400> SEQUENCE: 4
tctccggagg gctcgccatg ctgc                                             24

<210> SEQ ID NO 5
<211> LENGTH: 23
<212> TYPE: DNA
<213> ORGANISM: Artificial Sequence
<220> FEATURE:
<223> OTHER INFORMATION: IRS-1 antisens
```

```
<400> SEQUENCE: 5
tctccggagg gctcgccatg ctg                                          23

<210> SEQ ID NO 6
<211> LENGTH: 22
<212> TYPE: DNA
<213> ORGANISM: Artificial Sequence
<220> FEATURE:
<223> OTHER INFORMATION: IRS-1 antisens

<400> SEQUENCE: 6
tctccggagg gctcgccatg ct                                           22

<210> SEQ ID NO 7
<211> LENGTH: 21
<212> TYPE: DNA
<213> ORGANISM: Artificial Sequence
<220> FEATURE:
<223> OTHER INFORMATION: IRS-1 antisens

<400> SEQUENCE: 7
tctccggagg gctcgccatg c                                            21

<210> SEQ ID NO 8
<211> LENGTH: 20
<212> TYPE: DNA
<213> ORGANISM: Artificial Sequence
<220> FEATURE:
<223> OTHER INFORMATION: IRS-1 antisens

<400> SEQUENCE: 8
tctccggagg gctcgccatg                                              20

<210> SEQ ID NO 9
<211> LENGTH: 19
<212> TYPE: DNA
<213> ORGANISM: Artificial Sequence
<220> FEATURE:
<223> OTHER INFORMATION: IRS-1 antisens

<400> SEQUENCE: 9
tctccggagg gctcgccat                                               19

<210> SEQ ID NO 10
<211> LENGTH: 24
<212> TYPE: DNA
<213> ORGANISM: Artificial Sequence
<220> FEATURE:
<223> OTHER INFORMATION: IRS-1 antisens

<400> SEQUENCE: 10
ctccggaggg ctcgccatgc tgct                                         24

<210> SEQ ID NO 11
<211> LENGTH: 23
<212> TYPE: DNA
<213> ORGANISM: Artificial Sequence
<220> FEATURE:
<223> OTHER INFORMATION: IRS-1 antisens

<400> SEQUENCE: 11 tccgagggc tcgccatgct gct                                           23

<210> SEQ ID NO 12
```

```
<211> LENGTH: 22
<212> TYPE: DNA
<213> ORGANISM: Artificial Sequence
<220> FEATURE:
<223> OTHER INFORMATION: IRS-1 antisens

<400> SEQUENCE: 12
ccggagggct cgccatgctg ct                                      22

<210> SEQ ID NO 13
<211> LENGTH: 21
<212> TYPE: DNA
<213> ORGANISM: Artificial Sequence
<220> FEATURE:
<223> OTHER INFORMATION: IRS-1 antisens

<400> SEQUENCE: 13
cggagggctc gccatgctgc t                                       21

<210> SEQ ID NO 14
<211> LENGTH: 20
<212> TYPE: DNA
<213> ORGANISM: Artificial Sequence
<220> FEATURE:
<223> OTHER INFORMATION: IRS-1 antisens

<400> SEQUENCE: 14
ggagggctcg ccatgctgct                                         20

<210> SEQ ID NO 15
<211> LENGTH: 19
<212> TYPE: DNA
<213> ORGANISM: Artificial Sequence
<220> FEATURE:
<223> OTHER INFORMATION: IRS-1 antisens

<400> SEQUENCE: 15
gagggctcgc catgctgct                                          19

<210> SEQ ID NO 16
<211> LENGTH: 18
<212> TYPE: DNA
<213> ORGANISM: Artificial Sequence
<220> FEATURE:
<223> OTHER INFORMATION: IRS-1 antisens

<400> SEQUENCE: 16
agggctcgcc atgctgct                                           18

<210> SEQ ID NO 17
<211> LENGTH: 16
<212> TYPE: DNA
<213> ORGANISM: Artificial Sequence
<220> FEATURE:
<223> OTHER INFORMATION: IRS-1 antisens

<400> SEQUENCE: 17
ggctcgccat gctgct                                             16

<210> SEQ ID NO 18
<211> LENGTH: 15
<212> TYPE: DNA
<213> ORGANISM: Artificial Sequence
<220> FEATURE:
<223> OTHER INFORMATION: IRS-1 antisens

<400> SEQUENCE: 18
```

```
gctcgccatg ctgct                                                    15

<210> SEQ ID NO 19
<211> LENGTH: 14
<212> TYPE: DNA
<213> ORGANISM: Artificial Sequence
<220> FEATURE:
<223> OTHER INFORMATION: IRS-1 antisens

<400> SEQUENCE: 19
ctcgccatgc tgct                                                     14

<210> SEQ ID NO 20
<211> LENGTH: 13
<212> TYPE: DNA
<213> ORGANISM: Artificial Sequence
<220> FEATURE:
<223> OTHER INFORMATION: IRS-1 antisens

<400> SEQUENCE: 20
tcgccatgct gct                                                      13

<210> SEQ ID NO 21
<211> LENGTH: 12
<212> TYPE: DNA
<213> ORGANISM: Artificial Sequence
<220> FEATURE:
<223> OTHER INFORMATION: IRS-1 antisens

<400> SEQUENCE: 21
cgccatgctg ct                                                       12

<210> SEQ ID NO 22
<211> LENGTH: 25
<212> TYPE: DNA
<213> ORGANISM: Artificial Sequence
<220> FEATURE:
<223> OTHER INFORMATION: Scramble phosphorothioate oligonucleotide

<400> SEQUENCE: 22
tggacctctg gagctctcga cgtgc                                         25

<210> SEQ ID NO 23
<211> LENGTH: 20
<212> TYPE: DNA
<213> ORGANISM: Artificial Sequence
<220> FEATURE:
<223> OTHER INFORMATION: Primer for h-VEGFA

<400> SEQUENCE: 23
gagggcagaa tcatcacgaa                                               20

<210> SEQ ID NO 24
<211> LENGTH: 20
<212> TYPE: DNA
<213> ORGANISM: Artificial Sequence
<220> FEATURE:
<223> OTHER INFORMATION: Primer for h-VEGFA
```

```
<400> SEQUENCE: 24
tgctgtcttg ggtgcattgg                                               20

<210> SEQ ID NO 25
<211> LENGTH: 20
<212> TYPE: DNA
<213> ORGANISM: Artificial Sequence
<220> FEATURE:
<223> OTHER INFORMATION: Primer for h-GAPDH

<400> SEQUENCE: 25
tgaaggtcgg agtcaacgga                                               20

<210> SEQ ID NO 26
<211> LENGTH: 20
<212> TYPE: DNA
<213> ORGANISM: Artificial Sequence
<220> FEATURE:
<223> OTHER INFORMATION: Primer for h-GAPDH

<400> SEQUENCE: 26
cattgatgac aagcttcccg                                               20

<210> SEQ ID NO 27
<211> LENGTH: 20
<212> TYPE: DNA
<213> ORGANISM: Artificial Sequence
<220> FEATURE:
<223> OTHER INFORMATION: Primer for m-VEGFA

<400> SEQUENCE: 27
ttgtccaaga tccgcagacg                                               20

<210> SEQ ID NO 28
<211> LENGTH: 20
<212> TYPE: DNA
<213> ORGANISM: Artificial Sequence
<220> FEATURE:
<223> OTHER INFORMATION: Primer for m-VEGFA

<400> SEQUENCE: 28
tcggtctttc cggtgagagg                                               20

<210> SEQ ID NO 29
<211> LENGTH: 20
<212> TYPE: DNA
<213> ORGANISM: Artificial Sequence
<220> FEATURE:
<223> OTHER INFORMATION: Primer for m-GAPDH

<400> SEQUENCE: 29
agctcactgg catggccttc                                               20

<210> SEQ ID NO 30
<211> LENGTH: 20
<212> TYPE: DNA
<213> ORGANISM: Artificial Sequence
<220> FEATURE:
<223> OTHER INFORMATION: Primer for m-GAPDH

<400> SEQUENCE: 30
gaggtccacc accctgttgc                                               20
```

```
<210> SEQ ID NO 31
<211> LENGTH: 34
<212> TYPE: DNA
<213> ORGANISM: Artificial Sequence
<220> FEATURE:
<223> OTHER INFORMATION: Template (ELISA)

<400> SEQUENCE: 31
agcgataaga taggcctccc gagcggtacg acga                                  34
```